(12) United States Patent
Iott et al.

(10) Patent No.: US 8,252,030 B2
(45) Date of Patent: Aug. 28, 2012

(54) SPINAL IMPLANT CONNECTION ASSEMBLY

(75) Inventors: Andrew Iott, Villanova, PA (US); Adam Friedrich, Cinnaminson, NJ (US); Douglas Cahill, Levittown, PA (US); Brad Juchno, Yardley, PA (US)

(73) Assignee: Globus Medical, Inc., Audubon, PA (US)

( * ) Notice: Subject to any disclaimer, the term of this patent is extended or adjusted under 35 U.S.C. 154(b) by 366 days.

(21) Appl. No.: 12/401,198

(22) Filed: Mar. 10, 2009

(65) Prior Publication Data

US 2010/0234893 A1    Sep. 16, 2010

(51) Int. Cl.
*A61B 17/70* (2006.01)
(52) U.S. Cl. ........................... 606/278; 606/264
(58) Field of Classification Search ........... 606/250–278
See application file for complete search history.

(56) References Cited

U.S. PATENT DOCUMENTS

| | | | |
|---|---|---|---|
| 5,002,542 A | 3/1991 | Frigg | |
| 5,254,118 A | 10/1993 | Mirkovic | |
| 5,403,314 A | 4/1995 | Currier | |
| 5,466,237 A | 11/1995 | Byrd et al. | |
| 5,522,816 A | 6/1996 | Dinello et al. | |
| 5,545,163 A | 8/1996 | Miller et al. | |
| 5,562,662 A | 10/1996 | Brumfield et al. | |
| 5,609,592 A | 3/1997 | Brumfield et al. | |
| 5,885,285 A | 3/1999 | Simonson | |
| 6,004,322 A | 12/1999 | Bernstein | |
| 6,086,588 A | 7/2000 | Ameil et al. | |
| 6,187,005 B1 | 2/2001 | Brace et al. | |
| 6,280,443 B1 * | 8/2001 | Gu et al. | 606/264 |
| 6,485,491 B1 | 11/2002 | Farris et al. | |
| 6,565,567 B1 | 5/2003 | Halder | |
| 6,660,004 B2 | 12/2003 | Barker et al. | |
| 6,733,502 B2 * | 5/2004 | Altarac et al. | 606/266 |
| RE39,035 E | 3/2006 | Finn et al. | |
| 2005/0137594 A1 | 6/2005 | Doubler et al. | |
| 2005/0182409 A1 | 8/2005 | Callahan et al. | |
| 2006/0084989 A1 | 4/2006 | Dickinson et al. | |
| 2006/0106380 A1 | 5/2006 | Colleran et al. | |
| 2006/0149244 A1 | 7/2006 | Amrein et al. | |
| 2007/0043355 A1 | 2/2007 | Bette et al. | |
| 2007/0225707 A1 | 9/2007 | Wisnewski et al. | |
| 2008/0009862 A1 | 1/2008 | Hoffman | |
| 2008/0045955 A1 | 2/2008 | Berrevoets et al. | |
| 2008/0249570 A1 | 10/2008 | Carson et al. | |
| 2008/0294203 A1 | 11/2008 | Kovach et al. | |

FOREIGN PATENT DOCUMENTS

WO     WO 9401049     1/1994

* cited by examiner

*Primary Examiner* — Eduardo C Robert
*Assistant Examiner* — Tara Carter

(57) ABSTRACT

The present invention provides a connection assembly that can be used to securely connect a spinal implant to a bone anchor. In particular, the present invention preferably provides a spinal implant connection assembly that is able to securely connect the spinal implant to the anchors even when there is a variance in the angle and position of the anchors with respect to the spinal implant. Furthermore, the present invention provides a connection assembly with structure to increase the locking strength of the connection assembly.

8 Claims, 1 Drawing Sheet

SPINAL IMPLANT CONNECTION ASSEMBLY

FIELD OF THE INVENTION

The present invention relates generally to a connection assembly, and more particularly, to a variable angle spinal implant connection assembly.

BACKGROUND OF THE INVENTION

Spinal deformities, spinal injuries, and other spinal conditions may be treated with the use of spinal implants. Spinal implants are designed to support the spine and properly position the components of the spine. One such spinal implant includes an elongated rod and a plurality of bone anchors. The elongated rod is positioned to extend along one or more of the components of the spine and the bone anchors are attached to the spinal components at one end and secured to the elongated rod at the other end.

However, due to the anatomical structure of the patient, the spinal condition being treated, and, in some cases, surgeon preference, the bone anchors may be required to be positioned at various angles from the elongated rod. In addition, depending on the location of the bone anchor on the spinal column, the anchor may be required to be placed a distance away from the spinal implant. As a result, it can be difficult to obtain a secure connection between the elongated rod and the bone anchors.

As such, there exists a need for a connection assembly that is able to securely connect an elongated rod to bone anchors despite a variance in the angle and position of the bone anchor with respect to the rod.

SUMMARY OF THE INVENTION

The present invention provides a connection assembly that can be used to securely connect a spinal implant to a bone anchor. In particular, the present invention preferably provides a connection assembly that is able to securely connect the spinal implant to the anchor even when there is a variance in the angle and position of the anchor with respect to the spinal implant. Furthermore, in an embodiment of the present invention, the connection assembly provides additional structure to increase the locking strength of the connection assembly.

The connection assembly, in one embodiment, comprises a spinal implant positionable along a spinal column, an anchor member for engaging a vertebral body and a housing member that has an aperture for receiving a portion of the spinal implant and an opening for receiving the anchor member. Preferably, the housing member includes a channel extending through side surfaces of the housing member for receiving the spinal implant, an opening extending through an upper surface and a lower surface of the housing member for receiving the anchor member, a first clamping element for securing the anchor member in the opening of the housing member and a second clamping element for securing the spinal implant in the channel of the housing member.

Further areas of applicability of the present invention will become apparent from the detailed description provided hereinafter. It should be understood that the detailed description and specific examples, while indicating the preferred or exemplary embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiment(s) is merely exemplary in nature and is in no way intended to limit the invention, its application, or uses.

Figure 1:
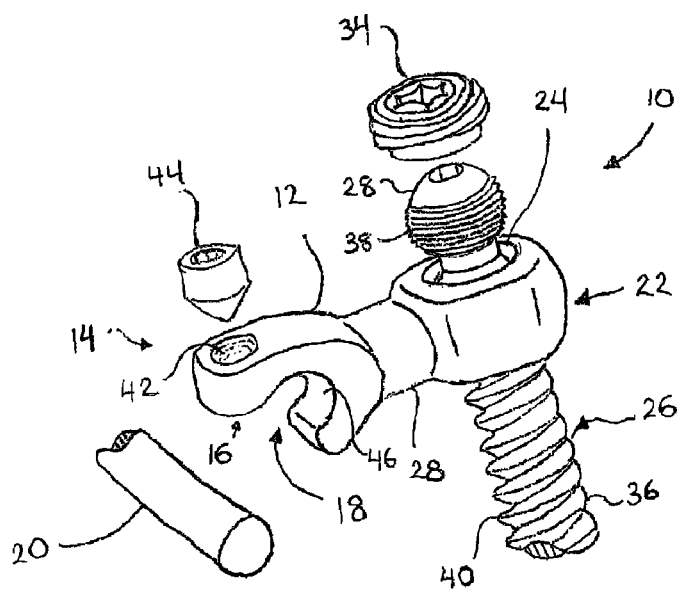
FIG. 1 is an exploded perspective view of one embodiment of a connection assembly.
Figure 2:
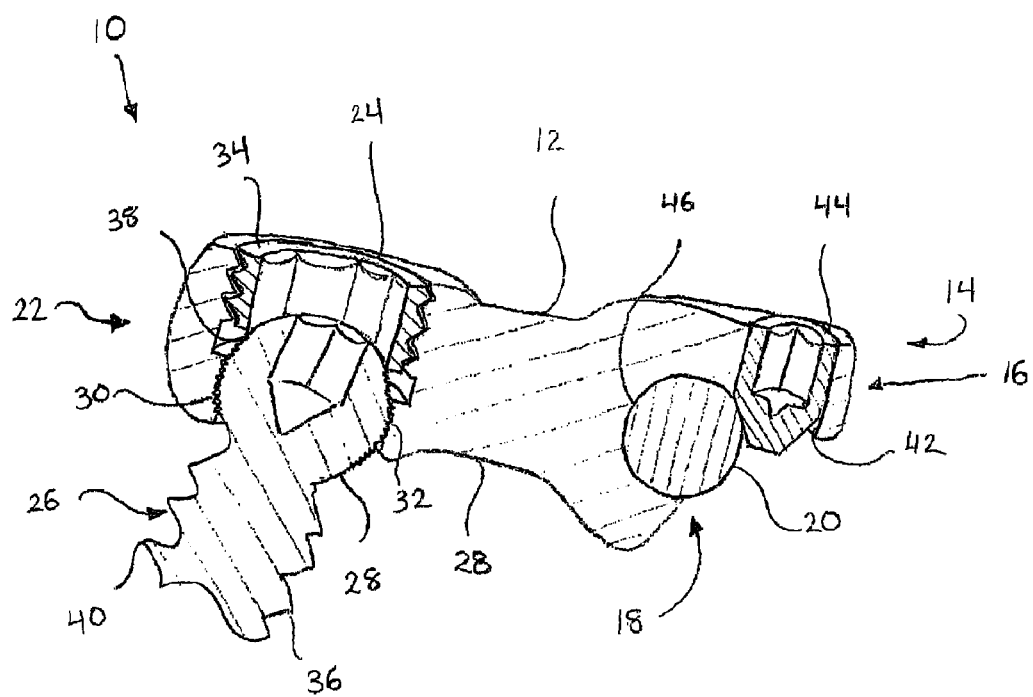
FIG. 2 is a cross sectional view of the connection assembly shown in FIG. 1.

With reference to FIGS. 1-2, a first embodiment of a connection assembly 10 is illustrated. The connection assembly 10 preferably includes a housing member 12 having, at a first end 14, a generally hook shaped end portion 16 defining a channel 18 configured and dimensioned for receiving at least a portion of a spinal implant 20, such as a spinal rod. At a second end 22, the housing member 12 includes a first opening 24 for receiving at least a portion of an anchor 26, such as a bone screw. The first end 14 and the second end 22 of the housing member 12 are joined by an elongated neck portion 28. The neck portion 28 preferably integrally joins the first end 14 and the second end 22 to form a unitary, one-piece housing member 12.

In an exemplary embodiment, the first opening 24 is configured and dimensioned to receive the anchor 26. The first opening 24 extends from an upper surface of the housing member 12 to a lower surface of the housing member 12 forming a through hole. Preferably, the first opening 24 is sized such that a head portion 28 of the anchor 26 can be received within the first opening 24 but cannot pass through the first opening 24. Looking at FIG. 2, a lower end 30 of the first opening 24 includes an arcuate section having a reduced diameter when compared to the diameter of the remainder of the opening 24. This reduced diameter section prevents the head portion 28 of the anchor 26 from passing through the lower end 30 of the first opening 24 and also serves as a complementary surface to the generally spherical head portion 28. In an exemplary embodiment, the first opening 24 includes a plurality ribs 32 extending along a portion thereof. Preferably, the ribs 32 are located along or neat the lower end 30 of the first opening 24. In another exemplary embodiment, at least a portion of the first opening 24 is threaded to receive a fastening member 34, but the first opening 24 can also be non-threaded.

The fastening member 34 is preferably a nut, as best seen in FIG. 1, but can be any type of fastening member including, but not limited to, an interference member or a cam member. In an exemplary embodiment, the fastening member 34 includes a threaded outer surface to engage the threading in the first opening 24 and a coupling for engaging a driver or other device for threading the fastening member 34 into the first opening 24.

As mentioned above, the anchor 26, in an exemplary embodiment, includes a head portion 28 and a shaft portion 36. In a preferred embodiment, the head portion 28 is generally spherical and includes a plurality of ridges 38 the shaft portion 36 includes a plurality of threads 40. The head portion 28 further includes a coupling for engaging a driver or other device for driving the anchor 26 into a vertebra. One of ordinary skill in the art would recognize that although only a bone screw is shown and described, the opening 24 is capable of receiving any number of anchors including, but not limited to, other orthopedic screws, hooks, bolts, or other similar bone anchoring devices.

In an exemplary embodiment, the housing member 12 also includes a second opening 42 at the first end 16 for receiving a securing member 44. The second opening 42 extends from an outer surface of the housing member 12 toward the channel 18 so that the second opening 42 is in fluid communication with the channel 18. At least a portion of the second opening 42 is preferably threaded to receive the securing member 44, but the second opening 42 can also be non-threaded.

The securing member 44 is preferably a threaded set screw, as best seen in FIG. 1, but can be any type of securing member including, but not limited to, a bolt, a pin, a shoe, an interference member, or a cam member. In an exemplary embodiment, the securing member 44 includes a coupling for engaging a driver or other device for threading the securing member 44 into the second opening 42. In another exemplary embodiment, the securing member 44 is captured in the second opening 42 preventing accidental disengagement of the securing member 44 from the housing member 12. The securing member 44 is captured in the second opening 42 by including an overhanging portion on the securing member 44 that abuts against the termination of the threading in the second opening 42.

In an exemplary use, the anchor 26 is passed shaft-first through the first opening 24 of the housing member 12 until the head portion 28 is located within the first opening 24. The anchor 26 can then be placed in the bone at a desired location taking into account the clinical situation, the patient anatomy, and the surgeon preference. It is important to note that since the head portion 28 is generally spherical, the housing member 12 can be rotated with respect to the anchor 24 in a ball and socket-like fashion. This provides three dimensional variability of the anchor 24 with respect to the housing member 12.

Independent of the anchor 26, the spinal implant 20 is typically placed along at least a portion of the length of the spinal column in an orientation and location that ideally suited for treatment, again taking into account the clinical situation, the patient anatomy, and the surgeon preference. Preferably, the spinal implant 20 is received in the channel 18 of the housing member 12. The channel 18 is configured and dimensioned to receive any portion of the spinal implant 20 allowing the connection assembly 10 to be place anywhere along the length of the spinal implant 20 or otherwise couple to the spinal rod 20 at any portion along its length.

Additionally, since the housing member 12 and anchor 26 are rotatable with respect to each other, even if the anchor 26 and the spinal implant 20 are angularly offset, the housing member 12 can be oriented to a desired position to connect the spinal implant 20 and the anchor 26. An advantage of this arrangement is that the anchor 24 and the spinal implant 20 can be connected without the need to contour the spinal implant 20. This simplifies the surgical procedure, reduces operating time, and prevents undue stress or damage to the spinal implant caused by the contouring. Once the desired orientation and positioning of the connection assembly 10 is achieved, the connection assembly 10 can be locked, securing the anchor 26 and the spinal implant 20.

To lock the connection assembly 10, the securing member 44 is threaded into the second opening 42 in the housing member 12 where it contacts and pushes the spinal implant 20 toward wall 46 of the channel 18. As best seen in FIG. 2, the spinal implant 20 is locked in place with respect to the housing member 12 when the implant 20 is lodged between the wall 46 of the channel 18 and the lower end of the securing member 44.

Independent of securing member 44, fastening member 34 is threaded into first opening 24 in the housing member 12 where it contacts and pushes the head portion 28 of the anchor 26 toward the lower end 30 of the first opening 20. As best seen in FIG. 2, the anchor 26 is locked in place with respect to the housing member 12 when the anchor 26 is lodged between the fastening member 34 and the lower end 30 of the first opening 20. As mentioned earlier, the head portion 28 of the anchor 26 includes a plurality of ridges 38. These members are configured and dimensioned to interdigitate with the ribs 32 when the head portion 28 is located in the lower end 30 of the first opening 20. Upon sufficient torque being applied to the fastening member 34, which, in turn, pushes on the head portion 28, the ridges 38 will deform around the ribs 32 forming a stronger, more secure "cold weld" between the anchor 26 and the housing member 12. This "cold weld" provides exceptional load bearing capabilities thereby increasing the versatility of the connection assembly. For example, because of the increased locking strength and load bearing capabilities, the locking assembly 10 can be used in a variety of high loading, high stress anatomical areas and procedures, such as, being used in the iliac crest area as well as with the S1 or upper sacral area of the spine.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A connection assembly for connecting a spinal implant to an anchor, the connection assembly comprising:
   a spinal implant positionable along at least a portion of the spinal column;
   an anchor having a head portion and a shaft portion, at least a portion of the shaft portion having threading for engaging a vertebra;
   a housing member for connecting the spinal implant and the anchor at any one of a plurality of angles, the housing member comprising:
      a channel for receiving the spinal implant;
      a securing member for securing the spinal implant in the channel;
      a first opening extending through top and bottom surfaces of the housing member for receiving the anchor;
      and a fastening member for securing the anchor in the first opening at any one of a plurality of angles relative to the housing member and the spinal implant,
   wherein the head portion includes a plurality of ridges and the opening includes a plurality of ribs
   wherein the plurality of ridges are capable of interdigitating with the plurality of ribs,
   wherein the plurality of ridges are deformable and are configured to deform around the plurality of ribs,
   wherein the plurality of ridges are deformable with respect to the plurality of ribs forming a cold weld,
   wherein the securing member is threaded into a second opening wherein it contacts and pushes the spinal implant toward wall of a channel of the housing wherein the securing member is captured in a second opening by including an overhanging portion on the securing member that abuts against the termination of the threading the second opening.

2. The connection assembly of claim 1, wherein the housing member includes the second opening for receiving the securing member and wherein at least a portion of the second opening is threaded.

3. The connection assembly of claim 1, wherein the securing member is a set screw.

4. The connection assembly of claim 1, wherein the channel is open on a side to allow insertion of the spinal implant in the channel.

5. The connection assembly of claim 1, wherein the housing member includes a yoke defining the channel.

6. The connection assembly of claim 1, wherein at least a portion of the opening is threaded and wherein the fastening member is a threaded nut.

7. The connection assembly of claim 1, wherein the securing member and the fastening member are separate components that operate independently.

8. A connection assembly for connecting a spinal implant to an anchor, the connection assembly comprising:

- a spinal implant positionable along at least a portion of the spinal column;
- an anchor having a head portion and a shaft portion, at least a portion of the shaft portion having threading for engaging a vertebra;
- a housing member for connecting the spinal implant and the anchor at any one of a plurality of angles, the housing member comprising:
  - a channel for receiving the spinal implant;
  - a securing member for securing the spinal implant in the channel;
  - a first opening extending through top and bottom surfaces of the housing member for receiving the anchor;
  - and a fastening member for securing the anchor in the first opening at any one of a plurality of angles relative to the housing member and the spinal implant, wherein the head portion includes a plurality of ridges and the opening includes a plurality of ribs wherein the plurality of ridges are capable of interdigitating with the plurality of ribs, wherein the plurality of ridges are deformable and are configured to deform around the plurality of ribs, wherein the securing member is captured in a second opening by including an overhanging portion on the securing member that abuts against the termination of the threading the second opening.

* * * * *